ized Patent [19]

Merz et al.

[11] 4,133,888
[45] Jan. 9, 1979

[54] ANALGESIC AND MORPHINE ANTAGONISTIC 2'-HYDROXY-2-(5-ISOXAZOLYL-METHYL)-6,7-BENZOMORPHANS AND SALTS THEREOF

[75] Inventors: Herbert Merz, Ingelheim am Rhein; Klaus Stockhaus, Bingen, both of Fed. Rep. of Germany

[73] Assignee: Boehringer Ingelheim GmbH, Ingelheim am Rhein, Fed. Rep. of Germany

[21] Appl. No.: 895,631

[22] Filed: Apr. 12, 1978

[30] Foreign Application Priority Data

Apr. 15, 1977 [DE] Fed. Rep. of Germany ....... 2716687

[51] Int. Cl.² .................. C07D 221/26; A61K 31/445
[52] U.S. Cl. ....................................... 424/267; 546/97
[58] Field of Search .................. 260/DIG. 13, 293.54, 260/307 H; 424/267

[56] References Cited

U.S. PATENT DOCUMENTS 3,499,906  3/1970  Robinson et al. ............... 260/293.54
3,823,150  7/1974  Merz et al. ....................... 260/293.54
3,853,889  12/1974  Monkovic et al. .............. 260/293.54

Primary Examiner—Henry R. Jiles
Assistant Examiner—Richard A. Schwartz
Attorney, Agent, or Firm—Hammond & Littell

[57] ABSTRACT

Compounds of the formula

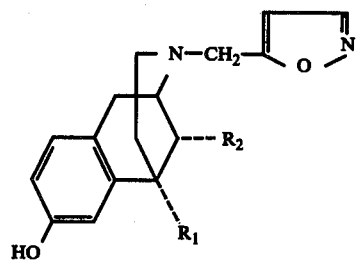

wherein $R_1$ is methyl, ethyl or propyl; and
$R_2$ is hydrogen, methyl or ethyl; and non-toxic, pharmacologically acceptable acid addition salts thereof; the compounds as well as their salts are useful as analgesics and morphine antagonists.

5 Claims, No Drawings

ANALGESIC AND MORPHINE ANTAGONISTIC 2'-HYDROXY-2-(5-ISOXAZOLYL-METHYL)-6,7-BENZOMORPHANS AND SALTS THEREOF

This invention relates to novel 2'-hydroxy-2-(5-isoxazolyl-methyl)-6,7-benzomorphans and non-toxic acid addition salts thereof, as well as to various methods of preparing these compounds.

THE PRIOR ART

Belgian Pat. No. 779,058 discloses certain analgesic and/or morphine-antagonistic 2'-hydroxy-2-(furyl-methyl)-6,7-benzomorphans. However, because of their relatively high toxicities these compounds have only a comparatively small therapeutic index, i.e. a relatively small spread between the median effective dose and the median lethal dose.

OBJECTS OF THE INVENTION

It is an object of the present invention to provide new 2'-hydroxy-6,7-benzomorphans which exhibit substantially the same activity spectrum than the prior art compounds, but which are significantly less toxic.

DESCRIPTION OF THE INVENTION

We have discovered that the above object is achieved by providing compounds of the formula

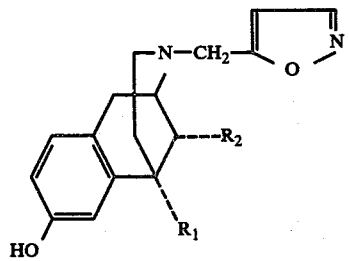

(I)

wherein $R_1$ is methyl, ethyl or propyl; and
$R_2$ is hydrogen, methyl or ethyl; and non-toxic, pharmacologically acceptable acid addition salts thereof.

When $R_2$ is methyl or ethyl, the compounds of the formula I occur as two different diastereoisomers, namely α and β-diastereoisomers. In the α-isomer the substituents $R_1$ and $R_2$ are in cis-configuration, whereas in the β-isomer they are in trans-configuration. As indicated by broken line bonds of $R_1$ and $R_2$ in formula I, the present invention relates to the α-diastereoisomers.

The compounds embraced by formula I occur as racemates or racemic mixtures and as dextro- or levorotatory optical antipodes.

Preferred embodiments are the 5,9-α-dialkyl-2'-hydroxy-2-(5-isoxazolyl-methyl)-6,7-benzomorphans of the formula I and their non-toxic, pharmacologically acceptable acid addition salts. Especially preferred are 5,9-α-dimethyl-2'-hydroxy-2-(5-isoxazolyl-methyl)-6,7-benzomorphan and its nontoxic, pharmacologically acceptable acid addition salts, and particularly the levorotatory optical antipodes thereof.

The compounds embraced by formula I may be prepared by the following methods:

Method A
By alkylating a norbenzomorphan of the formula

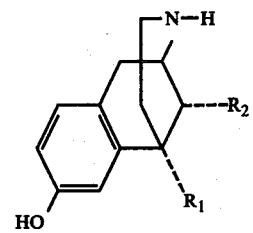

(II)

wherein $R_1$ and $R_2$ have the same meanings as in formula I, with a 5-isoxazolylmethyl compound of the formula

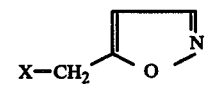

(III)

wherein X is a substituent which can be split off as anion, such as halogen, preferably chlorine, bromine or iodine, arylsulfonyloxy or alkylsulfonyloxy.

Because of its easy accessibility, 5-bromomethylisoxazole is particularly preferred as the alkylating agent of the formula III.

In order to utilize the relatively expensive starting compounds to the fullest extent, the alkylating agent of the formula III should be provided in the stoichiometric amount or preferably in excess thereover; in general, the desired effect is achieved by providing it in an amount corresponding to 10% above the equimolar amount. If the acidity of the acid HX released by the reaction is sufficient to form a salt with the norbenzomorphan of the formula II, it is advantageous, with a view toward a complete reaction, to perform the reaction in the presence of an acid-binding agent. For this purpose a wide variety of inorganic or organic bases may be used, such as carbonates, bicarbonates, oxides, hydroxides or amines. Particularly preferred are tertiary amines such as triethylamine, N,N-dicyclohexylethylamine, or inorganic bases such as sodium bicarbonate.

Although the employment of a solvent is not absolutely essential, it is advisable and advantageous to perform the reaction in the presence of an inert solvent. Suitable such solvents are, for example, hydrocarbons and certain halogenated hydrocarbons, as well as alcohols, ketones, ethers and aprotic solvents such as dimethylformamide and dimethylsulfoxide. Preferred are those solvents which have a boiling point range within a favorable reaction temperature, so that the reaction can be preformed at the reflux temperature of the reaction mixture. Mixtures of dimethylformamide and tetrahydrofuran have proved to be particularly well suited for this purpose.

The reaction temperature may be varied within wide limits; the lower limit is that temperature at which the rate of reaction is too slow, and the upper limit is the temperature at which interfering undersirable side-reactions predominate. Reaction temperatures between 50 and 150° C. are preferred.

Method B
By subjecting a 2'-acyloxy-2-(5-isoxazolyl-methyl)-6,7-benzomorphan of the formula

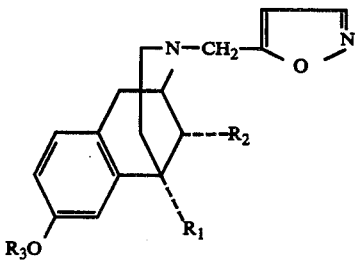

wherein $R_1$ and $R_2$ have the same meanings as in formula I, and $R_3$ is inorganic or organic acyl, to alkaline or, preferably, acid hydrolysis. For practical reasons, simple acyl radicals, especially acetyl or benzoyl, are preferred embodiments of $R_3$.

The ester cleavage in the 2'-position can be effected by a variety of known methods. The simplest method is an alkaline or, preferably, acid hydrolysis of the phenolic ester group; it is preferably performed in aqueous or aqueousalcoholic solution. The reaction temperature is variable within wide limits, but is most advantageously between 20 and 100° C.

Method C

By subjecting a 2'-alkoxy-2-(5-isoxazolyl-methyl)-6,7-benzomorphan of the formula

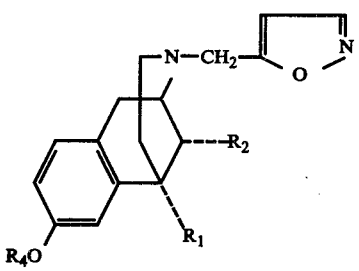

(V)

wherein $R_1$ and $R_2$ have the same meanings as in formula I, and $R_4$ is alkyl, preferably methyl, benzyl or methoxy-methyl, to ether cleavage in the 2'-position.

The ether cleavage can be effected by various known methods which depend upon the particular nature of $R_4$ and must be chosen so that the isoxazole ring remains unaffected. For instance, if $R_4$ is methoxy-methyl, it can be split off by treatment with a dilute mineral acid. If $R_4$ is methyl, a concentrated mineral acid, such as hydrobromic acid, is required to effect the ether cleavage. Particularly advantageous is the ether cleavage with boron tribromide.

The reaction products of methods A through C are isolated, purified and crystallized in the free base form or as their salts by conventional laboratory procedures.

The starting compounds of the formulas II and III are known compounds. The starting compounds of the formulas IV and V can be obtained by alkylating an O-acyl-norbenzomorphan or O-alkyl-norbenzomorphan with a compound of the formula III.

The compounds of the formula I are organic bases and therefore form acid addition salts with inorganic or organic acids. Example of non-toxic, pharmacologically acceptable acid addition salts are those formed with hydrochloric acid, hydrobromic acid, hydroiodic acid, hydrofluoric acid, sulfuric acid, phosphoric acid, nitric acid, acetic acid, propionic aid, butyric acid, valeric acid, oxalic acid, malonic acid, succinic acid, maleic acid, fumaric acid, lactic acid, pyruvic acid, tartaric acid, citric acid, malic acid, benzoic acid, p-hydroxybenzoic acid, salicylic acid, p-aminobenzoic acid, phthalic acid, cinnamic acid, ascorbic acid, 8-chlorotheophylline, methanesulfonic acid, ethanephosphonic acid or the like.

The following examples illustrate the present invention and will enable others skilled in the art to understand it more completely. It should be understood, however, that the invention is not limited solely to the particular examples given below.

EXAMPLE 1

5,9-α-Dimethyl-2'-hydroxy-2-(5-isoxazolyl-methyl)-6,7-benzomorphan and its hydrobromide, methanesulfonate and and hydrochloride by method A (a) A mixture consisting of 19.6 gm (0.09 mol) of 5,9-α-dimethyl-2'-hydroxy-6,7-benzomorphan, 11.8 gm (0.135 mol) of sodium carbonate, 16.2 gm (0.10 mol) of 5-bromoethylisoxazole, 120 ml of dimethylformamide and 200 ml of tetrahydrofuran was refluxed for 3.5 hours, while stirring. Thereafter, the solvent mixture was evaporated, first in a water aspirator pump vacuum and then on a water bath at 80°–90° C. The evaporation residue was shaken with a mixture of 250 ml chloroform and 150 ml water, and the chloroform phase was separated in a separator funnel, washed twice with 150 ml of water each, dried with sodium sulfate, treated with 5 gm of activated charcoal, filtered and evaporated in vacuo as above. 38gm of a brownish, syrupy evaporation residue were obtained, which were dissolved in a mixture of 35 ethanol and 7.0 ml of 68% hydrobromic acid. The mixture was stirred during the crystallization which soon began, until a thick crystalline slurry was formed which was kept overnight at 0° C. Thereafter, the crystallizate was separated by suction filtration, washed with a little ice-cold ethanol and then dried, first in the air and then at 80° C. in a drying chamber with circulating air. 31.7 gm (92.9% of theory) of the hydrobromide of the formula

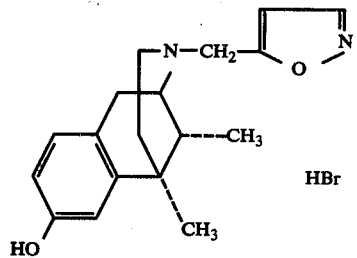

having a melting point of 166° C. were obtained. Recrystallization from a mixture of 100 ml of ethanol and 20 ml of water (storage at −20° C. overnight, suction filtration and drying, as above) yielded 28.8 gm of the hydrobromide with a melting point of 167° C.

(b) 28.8 gm (0.076 mol) of the hydrobromide obtained in (a) were dissolved in a mixture of 120 ml of methanol and 30 ml of water, and the solution was gradually (initially dropwise) admixed with 10.5 ml of concentrated ammonia while stirring, whereby a crystalline substance precipitated. Then, while continuing the stirring, an additional 90 ml of water were added, and the mixture was allowed to stand overnight at 0° C. Thereafter, the mixture was suction-filtered, and the filter cake was washed, first thoroughly with water and then with 50% methanol, again suction filtered and finally dried at 80° C. in a drying chamber with circulating air. 21.4 gm (94.4% of theory, based on the hydrobromide starting material) of 5,9-α-dimethyl-2'-hydroxy-2-(5-isoxazolyl-methyl)-6,7-benzomorphan with a melting point of 145°–147° C. were obtained. Recrystallization did not change the melting point of the product.

(c) 21.4 gm (0.072 mol) of the base were dissolved in 48 ml of ethanol while adding 7.2 gm (0.075 mol) of methanesulfonic acid thereto, whereby a crystalline substance soon began to separate out. The mixture was stirred until a thick crystal slurry had formed, which was then allowed to stand at 0° C. overnight. Thereafter, the mixture was suctionfiltered, and the filter cake washed with a mixture of ethanol and ether (1:1) and then dried, first in the air and then at 80° C. in a drying chamber with circulating air. 28.0 gm (98.6% of theory, based on the base starting material) of 5,9-α-dimethyl-2'-hydroxy-2-(5-isoxazolyl-methyl)-6,7-benzomorphan methanesulfonate with a melting point of 190°–192° C. were obtained. Recrystallization did not change the melting point of the product.

(d) 1.5 gm (0.005 mol) of the base were dissolved in 5 ml of ethanol while adding 2.5 ml of 2.5N ethanolic hydrochloric acid thereto. The solution was admixed with ether until it just began to turn cloudy, whereby a crystalline substance separated out. The product was isolated as described in (c) above, yielding 1.5 gm (89.5% of theory, based on the base starting material) of the hydrochloride of 5,9-α-dimethyl-2'-hydroxy-2-(5-isoxazolyl-methyl)-6,7-benzomorphan, m.p. 214° C. The melting point remained unchanged after recrystallization from ethanol/ether.

EXAMPLE 2

(−)-5,9-α-Dimethyl-2'-hydroxy-2-(5-isoxazolyl-methyl)-6,7-benzomorphan and its methanesulfonate by method A.

13.9 gm (0.064 mol) of (−)-5,9-α-dimethyl-2'-hydroxy-6,7-benzomorphan, 8.1 gm (0.095 mol) of sodium bicarbonate and 11.4 gm (0.070 mol) of 5-bromomethyl-isoxazole were reacted in a manner analogous to that described in Example 1, and the reaction product was isolated as there described. The syrupy evaporation residue of the chloroform extract (25 gm of the raw levo-rotatory free base) was dissolved in 40 ml of ethanol while adding 6.8 gm (0107 mol) of methanesulfonic acid thereto, whereby a crystalline substance began to separate out. The crystallization was aided by stirring and was brought to completion by allowing the crystal suspension to stand overnight at 0° C. Thereafter, the mixture was suction-filtered, and the filter cake was washed with ethanol/ether (1:1) and dried, first in the air and then at 80° C. in a drying chamber with circulating air. 19.8 gm (78.4% of theory) of (−)-5,9-α-dimethyl-2'-hydroxy-2-(5-isoxazolyl-methyl)-6,7-benzomorphan methanesulfonate, m.p. 188°–190° C., were obtained. Recrystallization from a mixture of 40 ml ethanol and 30 ml ether yielded 17.8 gm of the pure product, m.p. 189°–190° C., $[\alpha]^{25}_D = -95.0°$ (C = 1, methanol).

EXAMPLE 3

9-α-Ethyl-2'-hydroxy-2-(5-isoxazolyl-methyl)-5-methyl-6,7-benzomorphan and its methanesulfonate by method A 1.74 gm (0.0075 mol) of 9-α-ethyl-2'-hydroxy-5-methyl-6,7-benzomorphan, 0.95 gm (0.0113 mol) sodium bicarbonate and 1.34 gm (0.0083 mol) of 5-bromomethylisoxazole were reacted in a manner analogous to that described in Example 1, and the reaction product was isolated as there described. The syrupy evaporation residue of the chloroform extract was treated with 50 ml of ether, and the ether solution was decanted from insoluble side products and then evaporated. The residue, that is, the raw free base, was converted into its methanesulfonate in a manner analogous to that described in Example 2, yielding 2.0 gm (65.4% of theory) of the methanesulfonate, m.p. 188°–190° C. Recrystallization from methanol/ether yielded 1.7 gm of the salt, m.p. 188°–191° C.

EXAMPLE 4

5-Ethyl-2'-hydroxy-2-(5-isoxazolyl-methyl)-9-α-methyl-6,7-benzomorphan methanesulfonate by method A.

1.74 gm (0.0075 mol) of 5-ethyl-2'-hydroxy-9-α-methyl-6,7-benzomorphan, 0.95 gm (0.0113 mol) of sodium bicarbonate and 1.34 gm (0.0083 mol) of 5-bromomethyl-isoxazole were reacted in a manner analogous to that described in Example 3, and the free base reaction product was isolated and converted into the methanesulfonate in like manner. 2.2 gm (71.9% of theory) of 5-ethyl-2'-hydroxy-9-α-methyl-6,7-benzomorphan methanesulfonate, m.p. 211°–213° C., were obtained. Recrystallization from methanol/ether yielded 2.0 gm of the product with the same melting point.

EXAMPLE 5

5,9-α-Diethyl-2'-hydroxy-2-(5-isoxazolyl-methyl)-6,7-benzomorphan methanesulfonate by method A 1.84 gm (0.0075 mol) of 5,9-α-diethyl-2'-hydroxy-6,7-benzomorphan, 0.95 gm (0.0113 mol) of sodium bicarbonate and 1.34 gm (0.0083 mol) of 5-bromomethyl-isoxazole were reacted in a manner analogous to that described in Example 3, and the free base reaction product was isolated and converted into the methanesulfonate in like manner. 2.0 gm (63.1% of theory) of 5,9-α-diethyl-2'-hydroxy-2-(5-isoxazolyl-methyl)-6,7-benzomorphan methanesulfonate, m.p. 180°–182° C., were obtained. The melting point of the product did not change after recrystallization from methanol/ether.

EXAMPLE 6

2'-Hydroxy-2-(5-isoxazolyl-methyl)-5-methyl-6,7-benzomorphan hydrochloride by method A 1.53 gm (0.0075 mol) of 2'-hydroxy-5-methyl-6,7-benzomorphan, 0.95 gm (0.0113 mol) of sodium bicarbonate and 1.34 gm (0.0083 mol) of 5-bromomethyl-isoxazole were reacted in a manner analogous to that described in Example 1, and the reaction product was isolated as there described. The syrupy evaporation residue of the chloroform extract, that is, the raw free base product, was dissolved in 5 ml of ethanol while adding 3 ml of 2.5N ethanolic hydrochloric acid thereto, and the solution was admixed with ether until it just began to turn cloudy. A crystalline substance separated out which was collected and dried, yielding 1.7 gm (94.4% of theory) of 2'-hydroxy-2-(5-isoxazolyl-methyl)-5-methyl-6,7-benzomorphan hydrochloride, m.p. 211° C. The melting point did not change after recrystallization.

EXAMPLE 7

5-Ethyl-2'-hydroxy-2-(5-isoxazolyl-methyl)-6,7-benzomorphan by method A 1.63 gm (0.0075 mol) of 5-ethyl-2'-hydroxy-6,7-benzomorphan, 0.95 gm (0.0113 mol) of sodium bicarbonate and 1.34 gm (0.0083 mol) of 5-bromomethyl-isoxazole were reacted in a manner analogous to that described in Example 1, and the reaction product was isolated as there described. The evaporation residue of the chloroform extract was crystallized from a mixture of 10 ml of ether and 1 ml of acetone, and dried at 80° C. 1.5 gm of 5-ethyl-2'-hydroxy-2-(5-isoxazolyl-methyl)-6,7-benzomorphan were obtained. For further purification, the product was dissolved in about 80 ml of ethyl acetate, and the solution was treated with activated charcoal. After filtering off the charcoal, the filtrate was concentrated by evaporation to about 10 ml, whereupon the pure product, m.p. 186°-188° C., crystallized out. Yield: 1.15 gm (54.0% of theory).

EXAMPLE 8

2'-Hydroxy-2-(5-isoxazolyl-methyl)-5-(n-propyl)-6,7-benzomorphan by method A

Using a procedure analogous to that described in Example 6, 1.2 gm (53.8% of theory) of 2'-hydroxy-2-(5-isoxazolylmethyl)-5-(n-propyl)-6,7-benzomorphan, m.p. 178° C., were obtained from 1.74 gm (0.0075 mol) of 2'-hydroxy-5-(n-propyl) 6,7-benzomorphan, 0.95 gm (0.0113 mol) of sodium bicarbonate and 1.34 gm (0.0083 mol) of 5-bromomethyl-isoxazole.

The compounds of the present invention, that is, those embraced by formula I above and their non-toxic, pharmacologically acceptable acid addition salts, have useful pharmacodynamic properties. More particularly, they exert a therapeutically useful effect upon the central nervous system in warm-blooded animals, such as mice, especially analgesic and morphine-antagonistic activities, which were confirmed in the writhing test and the Haffner test. Pursuant to prevailing teachings, this agonistic/antagonistic activity spectrum points toward the absence of or a very low abuse potential. The same indication is suggested by the fact that 5,9-α-dimethyl-2'-hydroxy-2-(5-isoxazolyl-methyl)-6,7-benzomorphan is not capable of suppressing the abstinence symptoms in withdrawn morphine dependent rats and monkeys. The same compound is significantly superior, with respect to analgesic activity and therapeutic index, to the structurally most closely related known compound, 2-furfuryl-2'-hydroxy-5,9-α-dimethyl-6,7-benzomorphan. The same is true when the above-mentioned compound of this invention is compared with the known compound 2-(3-methyl-furfuryl)-2'-hydroxy-5,9-α-dimethyl-6,7-benzomorphan which, moreover, does not have the desired antagonistic component. Compared to pentazocine, another potent analgesic having the basic benzomorphan structure which is on the market, the above compound of the invention was found to have a similar agonistic/antagonistic activity spectrum, but to be far superior with respect to the therapeutic index.

The following table shows the relevant pharmacological data which substantiate the distinctions between the prior art compounds and the compound of the present invention discussed above.

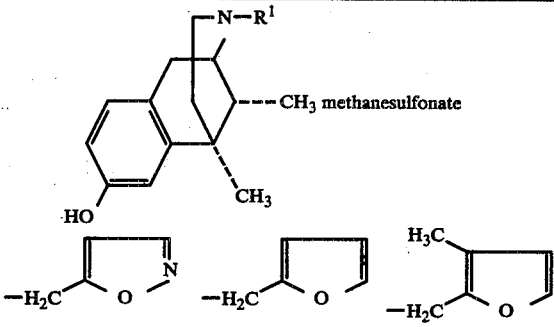

| R¹ | $-H_2C\text{-isoxazolyl}$ | $-H_2C\text{-furyl}$ | $-H_2C\text{-(3-methylfuryl)}$ | Pentazocine |
|---|---|---|---|---|
| Analgesia Writhing test mouse s.c. ED$_{50}$ mg/kg | 0.6 | 18 | 0.6 | 1.4 |
| Morphine-antagonism mouse (Nalorphine = 1) | 0.1 | 1 | inactive | 0.025 |
| Toxicity mouse, s.c. LD$_{50}$, mg/kg | 1080 | 292 | 305 | 220 |
| Index LD$_{50}$/ED$_{50}$ | 1800 | 16 | 508 | 157 |

For pharmaceutical purposes the compounds of the present invention are administered to warm-blooded animals peorally, parenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds according to the present invention is from 0.0083 to 1.67 mgm/kg body weight, preferably 0.016 to 0.33 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 9

Tablets

The tablet composition is compounded from the following ingredients:

| | |
|---|---|
| 5,9-α-Dimethyl-2'-hydroxy-2-(5-isoxazolyl-methyl)-6,7-benzomorphan methanesulfonate | 20.0 parts |
| Lactose | 120.0 parts |
| Corn starch | 50.0 parts |
| Colloidal silicic acid | 2.0 parts |
| Soluble starch | 5.0 parts |
| Magnesium stearate | 3.0 parts |
| Total | 200.0 parts |

Preparation

The benzomorphan derivative is intimately admixed with the lactose and the corn starch, the mixture is moistened with an aqueous 10% solution of the soluble starch, the moist mass is forced through a 1 mm-mesh screen, the resulting granulate is dried at 40° C., the dry granulate is admixed with the colloidal silicic acid, and the composition is compressed into 200 mgm-tablets in a conventional tablet making machine. Each tablet is an oral dosage unit composition containing 20 mgm of the benzomorphan derivative.

EXAMPLE 10

Coated pills

The pill core composition is compounded from the following ingredients:

| | |
|---|---|
| 5,9-α-Diethyl-2'-hydroxy-2-(5-isoxazolyl-methyl)-6,7-benzomorphan | 15.0 parts |
| Lactose | 100.0 parts |
| Corn starch | 95.0 parts |
| Colloidal silicic acid | 2.0 parts |
| Soluble starch | 5.0 parts |
| Magnesium stearate | 3.0 parts |
| Total | 220.0 parts |

Preparation

The ingredients are compounded in the same manner as in Example 9, and the composition is compressed into 220 mgm-bill cores which are subsequently coated with a thin shell consisting essentially of a mixture of sugar, talcum and gum arabic and finally polished with beeswax. Each coated pill; is an oral dosage unit composition containing 15 mgm of the benzomorphan derivative.

EXAMPLE 11

Suppositories

The suppository composition is compounded from the following ingredients:

| | |
|---|---|
| 5,9-α-Dimethyl-2'-hydroxy-2-(5-isoxazolyl-methyl)-6,7-benzomorphan hydrochloride | 10.0 parts |
| Lactose | 150.0 parts |
| Suppository base (e.g. cocoa butter) | 1540.0 parts |
| Total | 1700.0 parts |

Preparation

The benzomorphan derivative is intimately admixed with the lactose, and the mixture is blended with the aid of an immersion homogenizer into the suppository base which had previously been melted and cooled to about 40° C. 1700 mgm-portions of the composition are poured into cooled suppository molds and allowed to harden therein. Each suppository rectal dosage unit composition containing 10 mgm of the benzomorphan derivative.

EXAMPLE 12

Hypodermic solution

The solution is compounded from the following ingredients:

| | | |
|---|---|---|
| (-)-5,9-α-Dimethyl-2'-hydroxy-2-(5-isoxazolyl-methyl)-6,7-benzomorphan | | 1.0 parts |
| Sodium chloride | | 10.0 parts |
| Double-distilled water | q.s.ad | 1000.0 parts by vol. |

Preparation

The benzomorphan derivative and the sodium chloride are dissolved in the double-distilled water, the solution is filtered until free from suspended particles, and the filtrate is filled under aseptic conditions into 5 cc-ampules which are subsequently sterilized and sealed. Each ampule contains 1.0 mgm of the benzomorphan derivative, and its contents are an injectable dosage unit composition.

EXAMPLE 13

Drop solution

The solution is compounded from the following ingredients:

| | | |
|---|---|---|
| 5-Ethyl-2'-hydroxy-2-(5-isoxazolyl-methyl)-6,7-benzomorphan | | 0.70 parts |
| Methyl p-hydroxy-benzoate | | 0.07 parts |
| Propyl p-hydroxy-benzoate | | 0.03 parts |
| De-mineralized water | q.s.ad | 100.00 parts by vol. |

Preparation

The benzomorphan compound and the p-hydroxybenzoates are dissolved in the de-mineralized water, the solution is filtered, and the filtrate is filled into 100 cc-bottles. 10 ml of the solution are an oral dosage unit composition containing 70 mgm of the benzomorphan compound.

Any one of the other compounds of the present invention may be substituted for the particular active ingredient in Examples 9 through 13. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A racemic or optically active compound of the formula

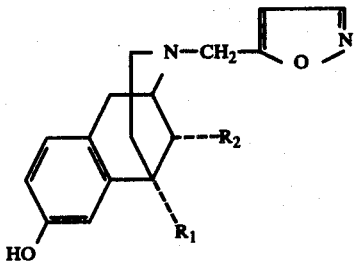

wherein
R₁ is methyl, ethyl or propyl; and
R₂ is hydrogen, methyl or ethyl;
or a non-toxic, pharmacologically acceptable acid addition salt thereof.

2. A compound of claim 1, which is 5,9-α-dimethyl-2'-hydroxy-2-(5-isoxazolyl-methyl)-6,7-benzomorphan or a nontoxic, pharmacologically acceptable acid addition salt thereof.

3. A compound of claim 1, which is (−)-5,9-α-dimethyl-2'-hydroxy-2-(5-isoxazolyl-methyl)-6,7-benzomorphan or a nontoxic, pharmacologically acceptable acid addition salt thereof.

4. A pharmaceutical dosage unit composition consisting essentially of an inert pharmaceutical carrier and an effective analgesic or morphine-antagonistic amount of a compound of claim 1.

5. The method of relieving pain or antagonizing the pharmacological effects of morphine in a warm-blooded animal, which comprises perorally, parenterally or rectally administering to said animal an effective analgesic or morphineantagonistic amount of a compound of claim 1.

* * * * *